(12) United States Patent
Cosgrove et al.

(10) Patent No.: US 8,133,690 B2
(45) Date of Patent: Mar. 13, 2012

(54) METHOD FOR INHIBITING THE FORMATION OF SET1 FAMILY CORE COMPLEXES

(75) Inventors: Michael S. Cosgrove, Syracuse, NY (US); Anamika Patel, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 12/509,874

(22) Filed: Jul. 27, 2009

(65) Prior Publication Data

US 2010/0022002 A1    Jan. 28, 2010

Related U.S. Application Data

(60) Provisional application No. 61/083,560, filed on Jul. 25, 2008.

(51) Int. Cl.
*G01N 33/48* (2006.01)
*G01N 33/567* (2006.01)

(52) U.S. Cl. .......................................... 435/7.21; 436/63

(58) Field of Classification Search .................. None
See application file for complete search history.

(56) References Cited

OTHER PUBLICATIONS

Patel et al, JBC 283: 32158-61, 2008, IDS, item 1,filed Aug. 5, 2009.*
Dou et al (Nat. Stru. Mol. Bio 13:713-719, 2006, IDS, item 5, filed Aug. 5, 2009.*
Patel et al., Structure of WDR5 Bound to Mixed Lineage Leukemia Protein-1 Peptide, The Journal of Biological Chemistry, Nov. 21, 2008, pp. 32158-32161, vol. 283, No. 47, The American Society for Biochemistry and Molecular Biology, Inc.
Patel et al., A Conserved Arginine-containing Motif Crucial for the Assembly and Enzymatic Activity of the Mixed Lineage Leukemia Protein-1 Core Complex, The Journal of Biological Chemistry, Nov. 21, 2008, pp. 32162-32175, vol. 283, No. 47, The American Society for Biochemistry and Molecular Biology, Inc.
Schuetz et al., Structural basis for molecular recognition and presentation of histone H3 by WDR5, The EMBO Journal, 2006, pp. 4245-4252, vol. 25, No. 18, European Molecular Biology Organization.
Couture et al., Molecular recognition of histone H3 by the WD40 protein WDR5, Nature Structural & Molecular Biology, Aug. 2006, pp. 698-703, vol. 13, No. 8, Nature Publishing Group.
Dou et al., Regulation of MLL1 H3K4 methyltransferase activity by its core components, Nature Structural & Molecular Biology, Aug. 2006, pp. 713-719, vol. 13, No. 8, Nature Publishing Group.
Ruthenburg et al., Histone H3 recognition and presentation by the WDR5 module of the MLL1 complex, Nature Structural & Molecular Biology, Aug. 2006, pp. 704-712, vol. 13, No. 8, Nature Publishing Group.
Trievel et al., WDR5, a complex protein, Nature Structural & Molecular Biology, Jul. 2009, pp. 678-680, vol. 16, No. 7, Nature America, Inc.

* cited by examiner

*Primary Examiner* — Misook Yu
*Assistant Examiner* — Lei Yao
(74) *Attorney, Agent, or Firm* — Hiscock & Barclay, LLP

(57) ABSTRACT

Disclosed in this specification is a method for inhibiting the formation of SET1 family core complexes. A guanidinium-containing molecule is used to competitively inhibit the binding of the N-SET region of a SET1 protein to WDR5, thus inhibiting the formation of the SET1 family core complex. The guanidinium-containing molecule may be, for example, an arginine-containing peptide. When bound to WDR5, the guanidinium moiety is bound between the F-133 and F-263 residues of the WDR5 when a crystal structure of the bound complex is obtained.

10 Claims, 10 Drawing Sheets

| SEQ ID. | Family | Start | Sequence | | | | | | | | | | | | | |
|---|---|---|---|---|---|---|---|---|---|---|---|---|---|---|---|---|
| SEQ ID NO. 1 | MLL1 | 3754 | N | E | P | P | L | N | P | H | G | S | A | R | A | E | V | H | L | R | K | S | A | F |
| SEQ ID NO. 2 | MLL2 | 5054 | L | P | L | M | I | N | P | T | G | C | A | R | S | E | P | K | I | L | T | H | Y | K |
| SEQ ID NO. 3 | MLL3 | 4699 | L | P | L | A | V | N | P | T | G | C | A | R | S | E | P | K | M | S | A | H | V | K |
| SEQ ID NO. 4 | MLL4 | 2500 | E | E | P | P | L | N | P | H | G | A | A | R | A | E | V | Y | L | R | K | C | T | F |
| SEQ ID NO. 5 | SET1a | 1484 | D | G | P | R | E | H | Q | T | G | S | A | R | S | E | G | Y | Y | P | I | S | K | K |
| SEQ ID NO. 6 | SET1b | 1874 | D | G | I | R | E | H | V | T | G | C | A | R | S | E | G | F | Y | T | I | D | K | K |

3745 → R (pointing to position in SEQ ID NO. 1)

Fig. 2

METHOD FOR INHIBITING THE FORMATION OF SET1 FAMILY CORE COMPLEXES

CROSS-REFERENCE TO RELATED APPLICATIONS

This application claims priority to and the benefit of U.S. provisional patent application Ser. No. 61/083,560, filed Jul. 25, 2008, which application is incorporated herein by reference in its entirety.

REFERENCE TO A SEQUENCE LISTING

This application refers to a "Sequence Listing" listed below, which is provided as an electronic document entitled "Sequence3033057.txt" (9 kb, created on Jul. 21, 2009), which is incorporated herein by reference in its entirety.

TECHNICAL FIELD

This disclosure relates, in one embodiment, to a method for inhibiting the formation of a SET1 family core complex. Advantageously, inhibition of the formation of the SET1 family core complex also inhibits the H3K4 dimethylation activity thereof.

BACKGROUND

Eukaryotes have evolved a complex system to regulate access to genomic information by packaging DNA into chromatin. Chromatin can adopt various levels of organization that regulate essential cellular activities such as transcription, DNA replication, recombination, and repair. The fundamental repeating unit of chromatin is the nucleosome in which base pairs of genomic DNA is wrapped around a disc-shaped octamer of histone proteins: H2A, H2B, H3 and H4. Nucleosome positioning on DNA is fundamentally involved in controlling gene access and is regulated in part by a diverse array of enzymes that introduce covalent post-translation modifications on histone proteins. An extensive array of histone modifications have been characterized, including lysine methylation. The large number of potential histone modification patterns provide cells with an enormous combinatorial potential for the precise regulation of gene function.

The combinatory complexity of histone modifications is further increased by histone lysine residues that can be mono-, di-, or trimethylated, each of which are correlated with distinct functional outcomes. One such lysine residue that is involved in gene regulation is the fourth residue on the H3 histone protein (H3K4). Several enzymes that regulate H3K4 methylation have been identified, all possessing the evolutionarily conserved SET domain, which is required for lysine methylation. Members of the SET1 family of proteins assemble into multisubunit complexes that regulate mono-, di- and trimethylation. The most studied human SET1 family member is the mixed lineage leukemia protein-1 (MLL1) which is required for the regulation of hox genes in hematopoiesis and development. Others member of the human SET1 family include MLL2, MLL3, MLL4, SET1a and SET1b.

Recently, it has been shown that the minimal complex required for di- and trimethylation of H3K4 includes MLL1, WDR5, RbBP5 and Ash2L, which together form the MLL1 core complex. The protein WDR5 has been shown to be critical for these interactions, as it bridges the catalytic SET domain of SET1 family proteins and the regulatory components of RbBP5 and Ash2L.

Overproduction of the MLL1 core complex leads to excessive di- and trimethylation of H3K4 which disrupts gene regulation. This, in turn, alters hematopoiesis and normal development and has been linked to certain types of leukemia, solid tumors, and psychotropic disorders, such as schizophrenia and bipolar disorders.

Therefore, a method for inhibiting the formation of SET1 family core complexes is desired. It is also desired to inhibit the H3K4 dimethylation (H3K4me2) activity of SET1 family core complexes by inhibiting the formation of such complex.

SUMMARY

This disclosure pertains to a method for inhibiting the formation of SET1 family core complexes. A guanidinium-containing molecule, such as an arginine-containing peptide, is provided which binds to the WDR5 protein at the same binding site utilized by the SET1 family proteins, thus inhibiting the SET1 family protein from successfully binding to WDR5. In this fashion the formation of the SET1 family core complex is inhibited.

BRIEF DESCRIPTION OF THE DRAWINGS

The present subject matter is disclosed with reference to the accompanying drawings, wherein:

FIG. 2 is a table depicting various Win motifs found in human SET1 proteins;

The examples set out herein illustrate several embodiments but should not be construed as limiting the scope of the claims in any manner.

DETAILED DESCRIPTION

Applicants have discovered specific regions on both the WDR5 protein and the N-SET domain of SET1 proteins where the two proteins bind to one another during the formation of a SET1 family core complex. An artificial peptide sequence is provided which mimics the binding region in the N-SET domain. This peptide binds to the corresponding specified region on WDR5, thus occupying the binding site where the SET1 protein would otherwise bind. In this fashion the binding of WDR5 and the SET1 protein is inhibited which decreases the formation of the SET1 family core complex. The results of this investigation will be presented first, followed by the rationales that lead to those results.

The Win Motif

Figure 1:
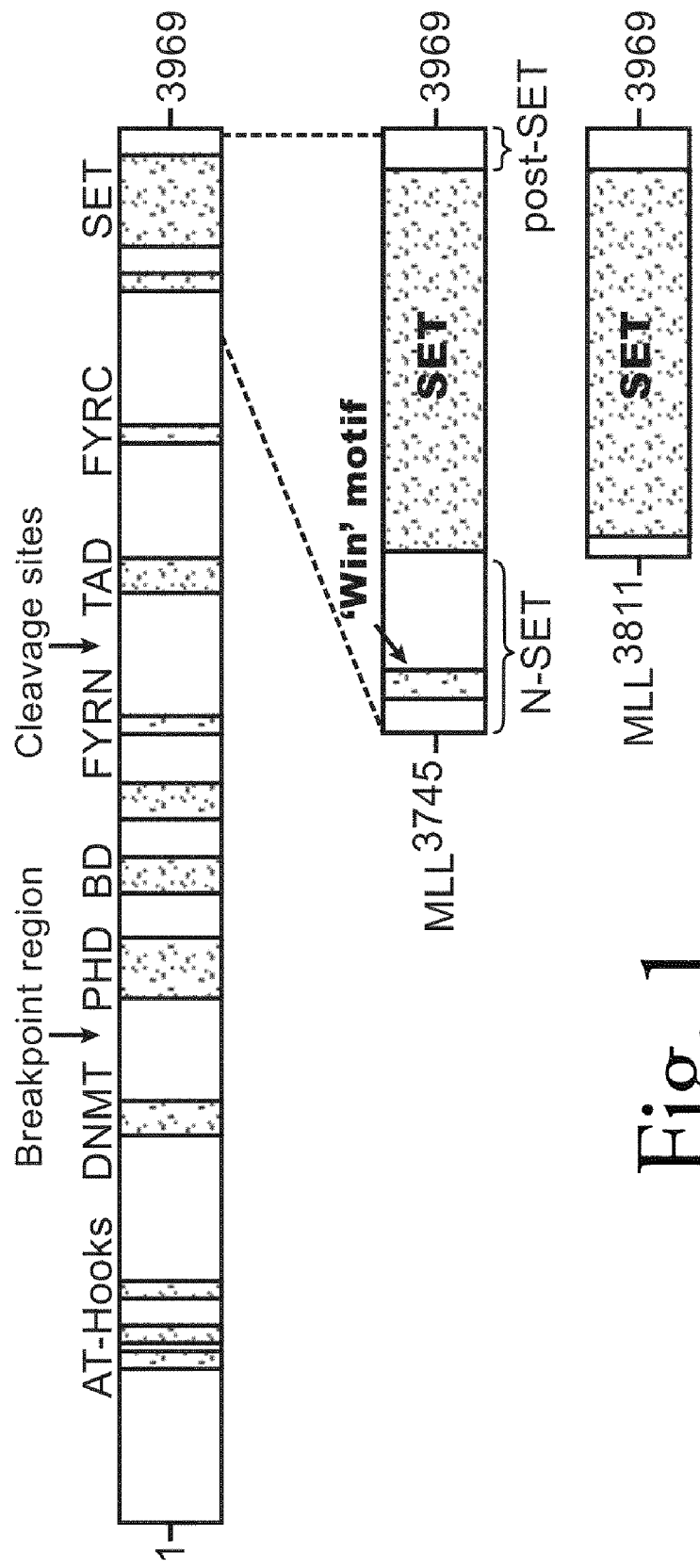
FIG. 1 is a depiction of the location of the Win motif relative to the N-SET and catalytic SET regions.

MLL1 is a large protein of 3,969 residues containing several conserved domains with functions that have been implicated in transcriptional regulation. The C-terminus of MLL1 is believed to interact with WDR5 somewhere over a domain encompassing residue numbers 3301-3969, a region which includes the N-SET region and the evolutionarily conserved SET domain. Prior to Applicants' discovery, the WDR5 binding site within this domain was unknown. Without wishing to be bound to any particular theory, applicants believe that the WDR5 protein binds to MLL1 in the semi-conserved N-SET region surrounding a strictly conserved arginine residue at R3765 in MLL1. Applicants refer to this motif as the WDR5 interaction motif, or "Win" motif. See FIG. 1. This motif has been found to be semi-conserved across multiple human SET1 family members. Examples of SET1 proteins include MLL1, MLL2, MLL3, MLL4, SETd1a and SETd1b. See FIG. 2 and SEQ ID NOS. 1-6. Since the Win motif is semi-conserved it follows that the present subject matter is applicable to all members of the SET1 family that include this Win motif.

The WDR5 Region

Figure 3A:
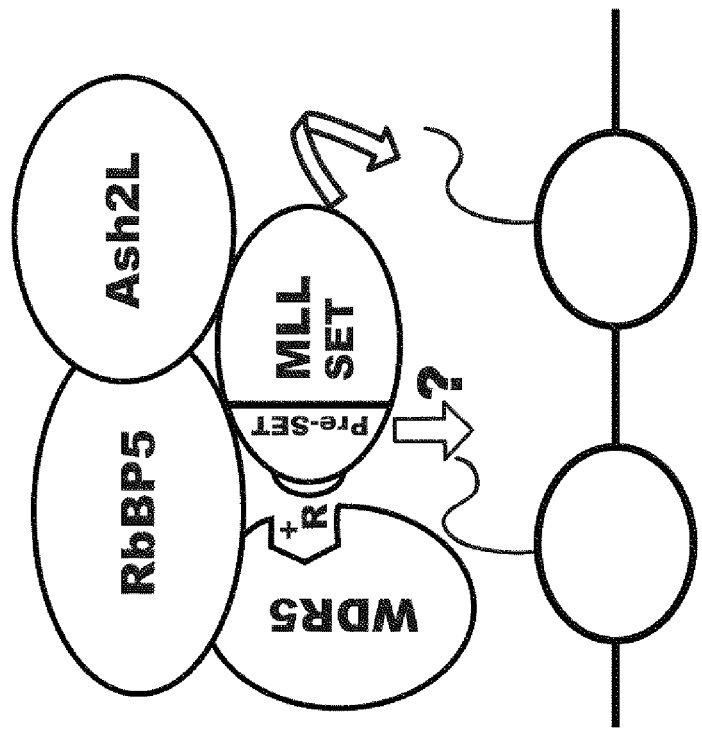
FIG. 3A and FIG. 3B are graphical depictions of the pre-existing model and the new model for the mode of methylation of SET1 family core complexes.
Figure 3B:
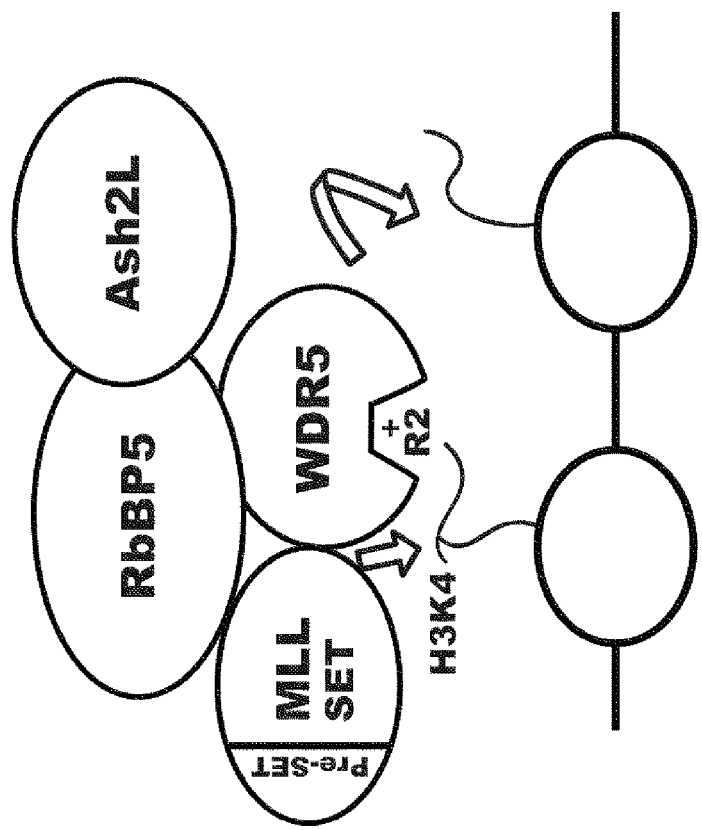

WDR5 is a common component of complexes that contain members of the SET1 family of H3K4 methyltransferases and is formed of seven WD40 repeats. Applicants have found that there is a corresponding binding site on WDR5 configured to bind to the Win motif found in the N-SET region of SET1 proteins. Unexpectedly, the binding site on WDR5 is the same site that was previously shown to bind to histone H3. The pre-existing model, shown in FIG. 3A, predicts that it should not be possible to inhibit the formation of the SET1 family core complex by blocking this binding site on WDR5. However, applicants have unexpectedly discovered that this pre-existing model is not correct. Without wishing to be bound to any particular theory, applicants suggest the new model shown in FIG. 3B provides a useful construct to understand their observations. In this new model, the arginine-containing Win motif in the SET1 protein binds to a corresponding region on WDR5. Applicants have discovered that blocking this WDR5 binding site with a competitive inhibitor disrupts the binding of a SET1 family protein to WDR5, thus inhibiting the formation of the SET1 family core complex. For example, the peptide may inhibit the binding of MLL1 to WDR5, thus inhibiting the formation of the MLL1 core complex. Since the formation of the SET1 family core complex is inhibited, the corresponding biological activity—dimethylation—is likewise suppressed.

Structural and functional results indicate that the arginine residue in the N-SET region of SET1 proteins interacts with the same arginine binding pocket of WDR5 that was previously shown to bind to R-2 of histone H3. Ruthenberg, *Nat. Struct. Mole. Biol.* 13, 704-712 (2006). This presents a paradox—how does WDR5 simultaneously interact with SET1 proteins and histone H3 if they both bind to the same site on WDR5? Although this presents an interesting dilemma for scientists, such an intellectual challenge does not touch on one's ability to inhibit the formation of SET1 family core complexes in accordance with the present teachings.

The Inhibitor Peptide

Based on the above discovery, several peptides have been designed that may be used to inhibit the formation of SET1 family core complexes. Applicants believe the peptides selectively bind to the N-SET region of SET1 proteins without effecting the catalytic SET domain of such proteins. Such peptides generally follow the formula of SEQ ID NO. 7. To facilitate their testing, the peptides have been generated with acetyl- and amide-capping groups the N and C termini, respectively, to eliminate the effects of unnatural N- and C-terminal charges on the binding. In other embodiments, no special end-capping is used. It should be understood that more residues, in addition to the six recited in SEQ ID NO. 7, can be included on either terminus of the sequence so long as such residues do not cause the resulting peptide to no longer inhibit the formation of SET1 family core complexes. Thus, peptides in accordance with SEQ ID NO. 7 are six or more residues in length.

$GX_1ARX_2X_3$  SEQ ID NO. 7
where $X_1$ = S, C or A $X_2$ = A or S $X_3$ = A or E In some embodiments, the G residue is preceded by a H or T residue.

$Z_1GX_1ARX_2X_3$  SEQ ID NO. 8
where $Z_1$ = H or T $X_1$ = S, C or A $X_2$ = A or S $X_3$ = A or E

Examples of Peptides with Six or More Residues

| Parent SET1 protein | SEQUENCE | SEQUENCE ID NO. |
|---|---|---|
| General | $GX_1ARX_2X_3$ | SEQ ID NO. 7 |
| MLL1 | GSARAE | SEQ ID NO. 9 |
| MLL1 variant | GSARAA | SEQ ID NO. 10 |
| MLL2 | GCARSE | SEQ ID NO. 11 |
| MLL3 | GCARSE | SEQ ID NO. 11 |
| MLL4 | GAARAE | SEQ ID NO. 12 |
| SET1a | GSARSE | SEQ ID NO. 13 |
| SET1b | GCARSE | SEQ ID NO. 14 |

Other suitable peptides are eight or more residues in length. Such peptides are also examples of peptides that fall under the scope of SEQ ID NO. 7 but, for the sake of brevity, have been omitted from the list of examples of peptides with six or more residues. One such embodiment includes residue $Z_1$ described elsewhere in this specification.

$GX_1ARX_2X_3X_4X_5$  SEQ ID NO. 15
where $X_1$ = S, C or A $X_2$ = A or S

```
             -continued
    X3 = A or E

X4 = V, P or G

X5 = H, Y, F or K

GX1ARX2X3X4Y1                SEQ ID NO. 16
where X1 = S, C or A

X2 = A or S

X3 = A or E

X4 = V, P or G

Y1 = H, Y or F
```

Eight or More Residues

| | | |
|---|---|---|
| General | GX1ARX2X3X4X5 | SEQ ID NO. 15 |
| General | GX1ARX2X3X4Y1 | SEQ ID NO. 16 |
| General | GX1ARX2X3X4K  | SEQ ID NO. 17 |
| MLL1    | GSARAEVHL     | SEQ ID NO. 18 |
| MLL2    | GCARSEPK      | SEQ ID NO. 19 |
| MLL3    | GCARSEPK      | SEQ ID NO. 19 |
| MLL4    | GAARAEVY      | SEQ ID NO. 20 |
| SET1a   | GSARSEGY      | SEQ ID NO. 21 |
| SET1b   | GCARSEGF      | SEQ ID NO. 22 |

$X_4$ is a small hydrophobic residue such as V, P or G. In SEQ ID NO. 15 $X_5$ is H, Y, F or K. In one embodiment (SEQ ID NO. 16) the residue ($Y_1$) is an aromatic residue such as H, Y or F. In other embodiments (SEQ ID NO. 17) ($Y_1$) is a lysine residue. Such a lysine residue may hydrogen bond to a conserved Asp residue in WDR5.

In one embodiment, $X_3$ is E (SEQ ID NO. 23). Such peptides may be desired in certain circumstances since the corresponding position in the naturally occurring human sequences is high conserved (see FIG. 2). Nevertheless, laboratory experiments show bonding between the peptide and WDR5 with residues other than E are used.

```
GX1ARX2EX4X5                 SEQ ID NO. 23
where X1 = S, C or A

X2 = A or S

X4 = V, P or G

X5 = H, Y, F or K
```

In certain embodiments, the inhibitor peptide is produced synthetically. Current synthetic methods are generally limited to producing peptides with fewer than one hundred amino acids. In one embodiment, the Win peptide is a synthetic peptide with fewer than one hundred residues. In certain embodiments, and to reduce product costs as well as avoid potential complications caused by the inclusion of too many residues, it may be desirable to reduce the total residue count below fifty residues. In yet another embodiment, the peptide has fewer than twenty residues. Peptides that are longer than one hundred residues might be produced using non-synthetic technology, such as recombinant technology. Such longer peptides are considered to fall within the scope of this invention.

As is known in the art, degree of inhibition of the SET1 family core complex can be measured using known techniques, such as analytical ultracentrifugation methods. Suitable ultracentrifugation methods include sedimentation equilibrium analysis and sedimentation velocity analysis. Likewise, degree of inhibition of the H3K4 activity of a SET1 sample can be measured using customary enzyme activity techniques. In both cases, inhibition is measured relative to an identical sample that lacks the inhibiting peptide. The degree of inhibition was found to be dependent on the dose of the Win peptide, consistent with a competitive inhibitor.

In another embodiment, a molecule other than a peptide is used as the inhibiting agent. Such a molecule includes a guanidinium moiety that is bound between the F-133 and F-263 residues of the WDR5 when a crystal structure of the bound complex is obtained. In this manner, the binding site used by WDR5 is occupied by the guanidinium moiety, thus preventing the SET1 protein from binding. The chemical structure of the remainder (non-guanidinium portion) of the molecule can be any suitable structure that does not interfere with, and preferable enhances, the binding of the molecule into the identified binding site.

Model of Operation

Evidence that supports the new model has been gathered by various methods. Although not wishing to be bound by any particular theory, the following experimental observations may prove useful in designing SET1 family core complex inhibitors that fall under the scope of this invention.

To demonstrate that the binding site on WDR5 had been properly identified WDR5 was co-crystallized with a Win peptide consisting of amino acid residues 3762-3773 of MLL1 (GSARAEVHLRKS, SEQ ID NO. 24). The x-ray structure of the complex was determined at 1.72-Å resolution. The overall structure of WDR5 is highly similar to that of previously reported structures of WDR5 bound to histone H3. Like previously reported structures of WDR5, the present structure is formed by seven WD40 repeats or β-propeller blades that are organized around a central cavity. A water-filled tunnel connects the two openings of the cavity at the top and bottom of the structure with the top opening having a smaller diameter. Previous structures of WDR5 bound to H3 histones show that the N terminus of histone H3 forms a partial $3_{10}$-helix when bound to the smaller opening at the top of WDR5, which is anchored by the insertion of H3R2 into the central tunnel. In the present structure, the initial difference electron density map clearly identifies the location of the Win peptide SEQ ID NO. 24 which, consistent with our prediction, is located in the same position as suggested previously for histone H3 binding. Nine residues from the N terminus could be modeled into the density, with the last three residues of the C terminus being disordered. Consistent with the tight binding observed in ITC experiments, the electron density from simulated annealing $F_o$-$F_c$ omit maps covers most of the modeled peptides, even when contoured at 3σ. Additional information concerning this crystal structure is available in J. Bio. Chem.; v, 283, no. 47, pp. 32158-32161, Nov. 21, 2008.

The N terminus of the Win peptide SEQ ID NO. 24, like histone H3 bound to WDR5, forms a $3_{10}$-helix that fits snuggly into the outer opening of the central cavity, like a cork in a bottle. Conserved SET1 residues GSARAE (SEQ ID NO. 25) all participate in the formation of the $3_{10}$-helix, which is stabilized by intramolecular i→i+3 main-chain hydrogen bonds between Ser-2 and Ala-5 and between Ala-3 and Glu-6. This configuration is further stabilized by an intramolecular hydrogen bond between the carboxylate side chain of Glu-6 and the amide nitrogen of Gly-1. This intramolecular hydrogen bond gives the sequence a cyclical conformation that allows the $3_{10}$-helix to fit precisely into the outer opening of the central cavity. Point mutation studies, discussed below, provide guidance concerning acceptable variations of this peptide sequence.

An extensive network of direct and water-mediated intermolecular hydrogen bonds and van der Waals interactions stabilizes the binding of the $3_{10}$-helix to the opening of the central cavity. In previous structures of WDR5 bound to histone H3, Asp-107 of WDR5 forms a salt bridge with the N terminus of histone H3 and coordinates a network of water molecules that fill part of the central cavity. In the present structure, these water molecules are displaced by Gly-1 and Ser-2 of the Win peptide SEQ ID NO. 7, which participate in multiple hydrogen bond and van der Waals interactions with Ala-47, Ala-65, Gly-89, Ile-90, and Asp-107. It is likely that these interactions account, in part, for the high affinity of WDR5 for the Win peptide. Indeed, the high quality of density at the N-terminal end of the peptide suggests that additional residues at the N terminus could show additional interactions. However, ITC binding experiments with a peptide containing six additional residues on the N terminus shows identical affinity with that of the shorter peptide used for crystallization, suggesting that the peptide used in this investigation includes many of the important interactions. It should therefore be understood that peptides such as SEQ ID NO. 24 and SEQ ID NO.25 may have additional residues incorporated on one or both termini so long as such residues do not impact the peptide's ability to inhibit the formation of the SET1 family core complex.

Ala-3 and Arg-4 of the Win peptide (SEQ ID NO. 24) occupy similar positions as Ala-1 and Arg-2 of the H3 histone in the previously reported H3-WDR5 complexes. The side chain of Arg-4 of the Win peptide inserts into the central tunnel of WDR5 and is stabilized by an extensive network of hydrogen bond, π-π and cation-π, and hydrophobic interactions with WDR5 residues: Ser-91, Phe-133, Ser-175, Ser-218, Cys-261, Phe-263, and Ile-305. As noted for Arg-2 of histone H3, it is likely that the sum of these interactions accounts for the majority of the binding energy between the Win peptide and WDR5, which explains why mutation of Arg-3765 in MLL1 is sufficient to abolish the assembly and dimethylation activity of the MLL1 core complex in vitro. This suggests a reason for the conservation of Arg-3765 in MLL1 orthologs and other SET1 family members. In addition, the guanidinium moiety of Arg-4 is sandwiched between the conserved aromatic side chains of Phe-133 and Phe-263 of WDR5, which are important for the interaction. This probably explains why the replacement of Phe-133 of MLL1 with alanine significantly diminishes the interaction between MLL1 and the WDR5-RbBP5-Ash2L sub-complex in vitro and in vivo.

Amino acids on the C-terminal side of Arg-4 in SEQ ID NO. 24 also participate in a number of intermolecular interactions with WDR5. Ala-5 of SEQ ID NO. 24 interacts with Ala-47 and Tyr-260 of WDR5. The aromatic ring of Tyr-260 lines the outer edge of the central cavity and makes van der Waals contacts with Ala-5, Glu-6, and Val-7 of the Win peptide. Glu-6 of the Win peptide occupies a similar position as Lys-4 of the histone H3 in previous structures with WDR5. However, in contrast to previous structures in which the side chain of H3K4 was poorly ordered, the side chain of Glu-6 is well ordered in the present structure. This is due to direct and water-mediated intramolecular hydrogen bonds involving the side chain carboxylate of Glu-6 and the main chain amides of Gly-1 and Val-7. This may explain the high sequence conservation of Glu-6 in SET1 family members. In addition, the carbonyl oxygen of Glu-6 forms a water-mediated hydrogen bond with the side-chain of Tyr-191.

The last two residues of the Win peptide SEQ ID NO. 24 that could be modeled into the density include His-8 and Leu-9, the latter of which was less ordered. The main chain of His-8 participates in water-mediated hydrogen bonds with Lys-259, whereas the side chain of His-8 forms hydrogen bonds, van der Waals, and T-stacking interactions with WDR5 residues: Phe-149, Asp-172, Pro-173, and Tyr-191. This results in the imidazole of His-8 being well ordered, even when contoured at 3-π. Leu-9 is less ordered than previous residues and does not appear to make any interactions with WDR5. It is likely that these newly observed interactions account in part for the greater affinity of the Win peptide when compared with previously published values for histone H3 binding to free WDR5. ITC measurements show that the Win peptide binds to WDR5 with an equilibrium dissociation constant $K_d$ of 1.7±0.1 µM, which is between 3- and 45-fold lower than that previously reported for the binding of dimethylated histone H3K4 peptides to WDR5 using a similar technique. However, the affinity observed in ITC experiments does not appear to completely recapitulate the full interaction surface between MLL1 and WDR5, which interact with a $K_d$ of ~0.12 µM in solution when measured by sedimentation velocity analytical ultracentrifugation. Nevertheless, the same Win peptide specifically inhibits the dimethylation activity of the MLL1 core complex by dissociating the catalytic SET domain of MLL1 from the regulatory WDR5-RbBP5-Ash2L subcomplex. These results are consistent with the hypothesis that the recognition of the arginine residue in the N-SET region by WDR5 is crucial for the interaction between WDR5 and MLL1. This interaction is essential for the assembly and activity of the SET1 family core complex.

Figure 4A:
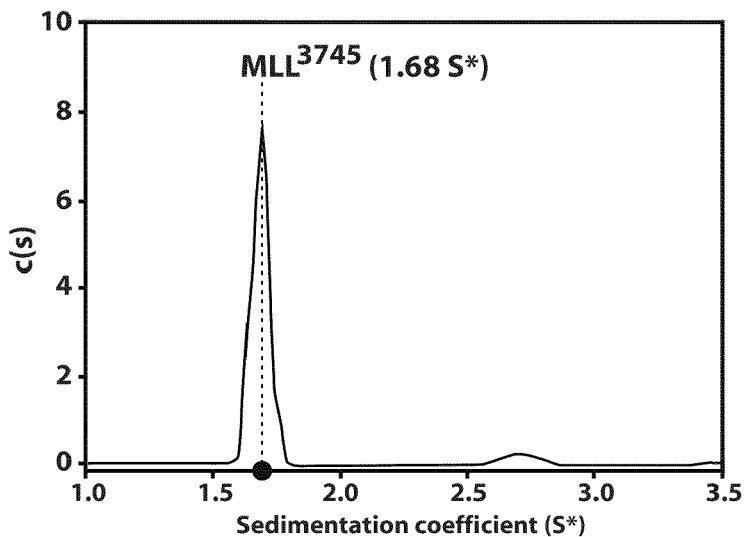
FIG. 4A, FIG. 4B and FIG. 4C are sedimentation velocity data for two MLL1 variants and WDR5.
Figure 4B:
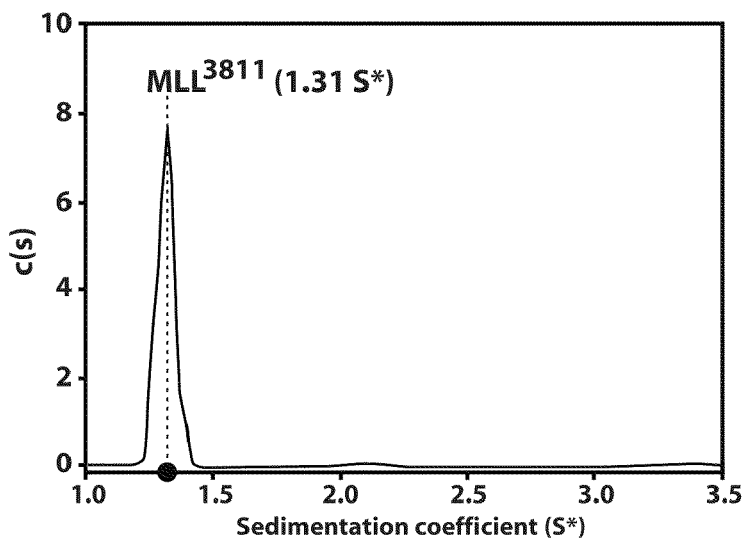
Figure 4C:
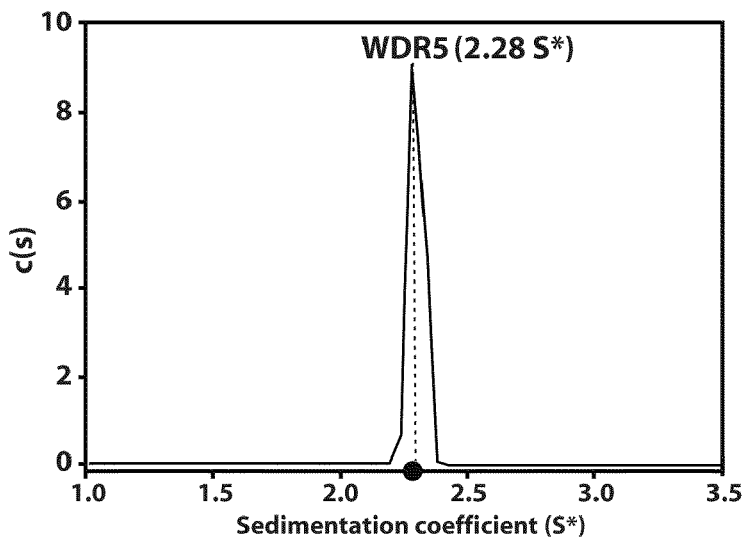

One polypeptide construct consisting of residues 3745-3969 of human MLL1 (henceforth $MLL^{3745}$, SEQ ID NO. 26) was made. This construct includes 66 amino acid residues of the N-set region followed by the conserved SET and post-SET domains. We believed this to be the minimal MLL SET domain construct required for the assembly of the full MLL1 core complex in vitro. A second polypeptide construct consisted of residues 3811-3969 (henceforth $MLL^{3811}$) and encompassed only the conserved SET and post-SET domains. Both constructs are catalytically active in methytransferase assays with histone H3 peptides compassing residues 1-20. Sedimentation velocity analyses were performed with each of the proteins individually and were fitted to a distribution of Lamm equation solutions to determine the diffusion-free sedimentation coefficient distribution (c(s)). The resulting data is depicted in FIG. 4A, FIG. 4B and FIG. 4C. $MLL^{3745}$, $MLL^{3811}$ and WDR5 showed sedimentation values of approximately 1.68, 1.31 and 2.28, respectively, corresponding to the values for the un-complexed species.

Figure 5A:
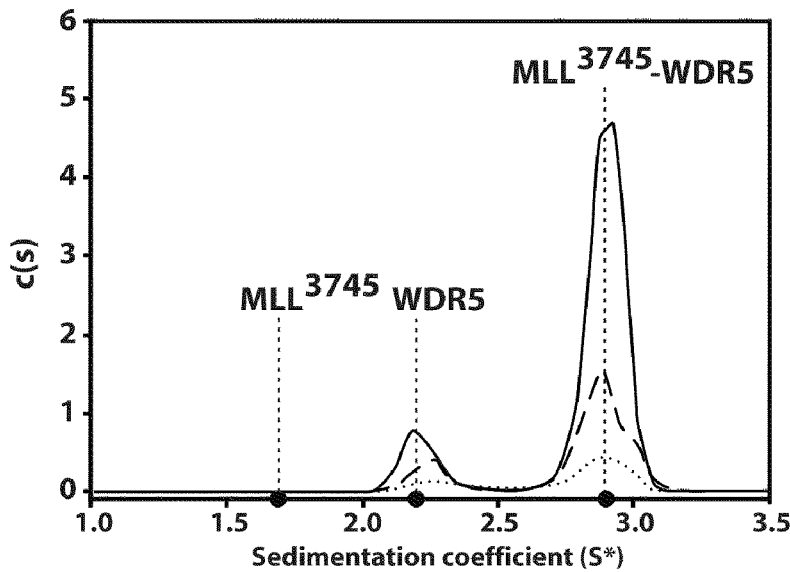
FIG. 5A and FIG. 5B show the sedimentation velocity data for the interaction of $MLL^{3745}$ with WDR5 and the lack of interaction of $MLL^{3811}$ with WDR5.

As shown in FIG. 5A, when $MLL^{3745}$ was mixed with WDR5 at a 1:1 stoichiometric ratio a complex is formed with an s* value of 2.87. This is within the expected range for a complex that would be formed when $MLL^{3745}$ and WDR5 bind.

Figure 5B:
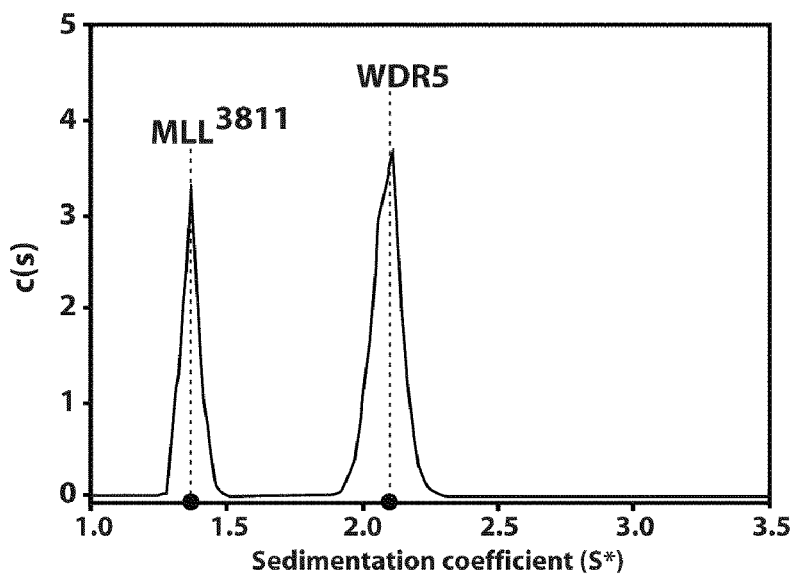

As shown in FIG. 5B, when MLL3811 was mixed with WDR5 at a 1:1 stoichiometric ratio no complex was formed. These two results indicate that the 66 residue N-SET region of MLL1, which was not present in MLL$^{3811}$, contains the sequences that are required for the interaction of WDR5 with MLL1.

Figure 6A:
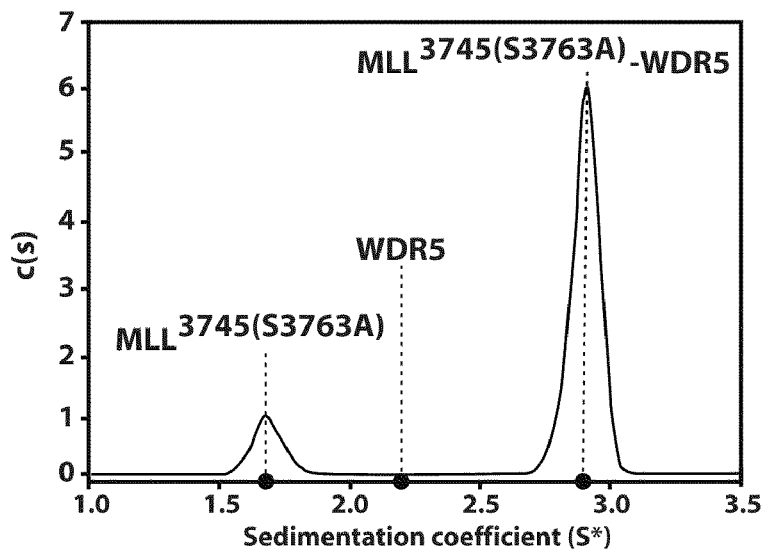
FIG. 6A, FIG. 6B and FIG. 6C show the sedimentation velocity data for the interaction of point-mutated $MLL^{3745}$ proteins with WDR5.
Figure 6B:
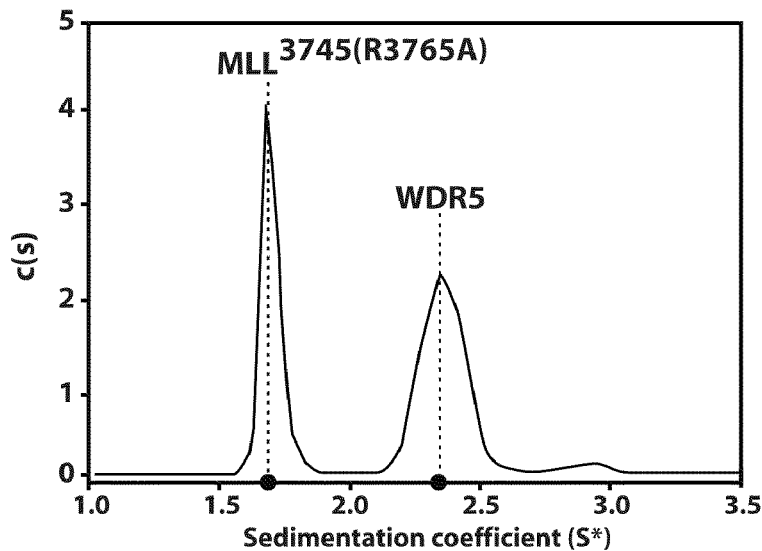
Figure 6C:
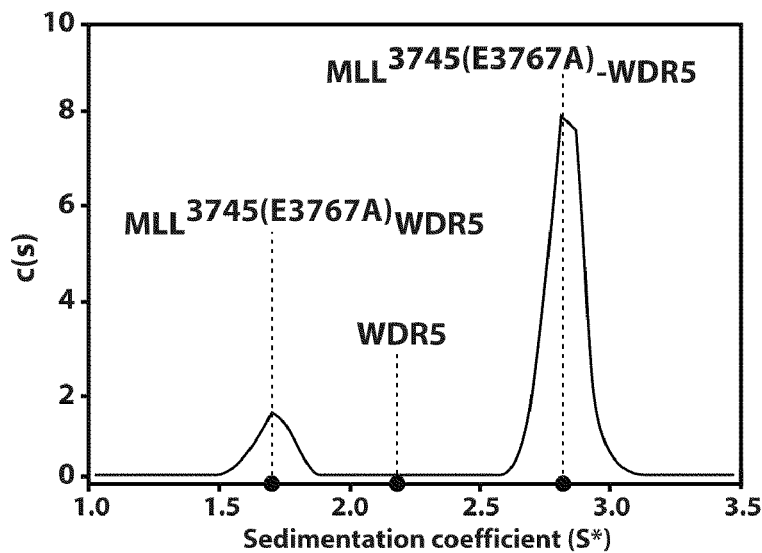

A sequence alignment study was performed to identify the key sequences in the N-SET region of various human SET1 family members that are important for binding. The results are presented in FIG. 1. Although the N-SET region is less conserved that the catalytic SET region, an 8 residue sequence was successfully identified with a higher degree of conservation in the first 6 residues. To determine which of these residues are important for the interaction of WDR5 and MLL1, select residues were individually replaced. Referring to SEQ ID NO. 26 (MLL$^{3745}$) the following residues were individually replaced with alanine and the resulting polypeptides were examined for their ability to bind to WDR5: S-19, R-21, E-23 (corresponding to S-3762, R-3765, E-3767 on MLL1). The results, shown in FIG. 6A-C, show that the serine and glutamine residues could successfully be replaced by alanine with only a modest effect on the binding with WDR5. However, replacement of the arginine residue showed that the polypeptide no longer bound to WDR5. No interaction was found with the MLL$^{3745}$ (R3765A) polypeptide even at 1:5 stoichiometric ratio.

Subsequent far-UV CD spectra suggested that the MLL$^{3745}$ (R3765A) polypeptide had a secondary structure that was substantially identical to that of MLL$^{3745}$. Additionally, the frictional coefficients derived from sedimentation velocity experiments are essentially unchanged relative to MLL$^{3745}$. These results suggest that is it the arginine residue itself that is important for binding, rather than a structural change that is induced by changing the residue.

Figure 8:
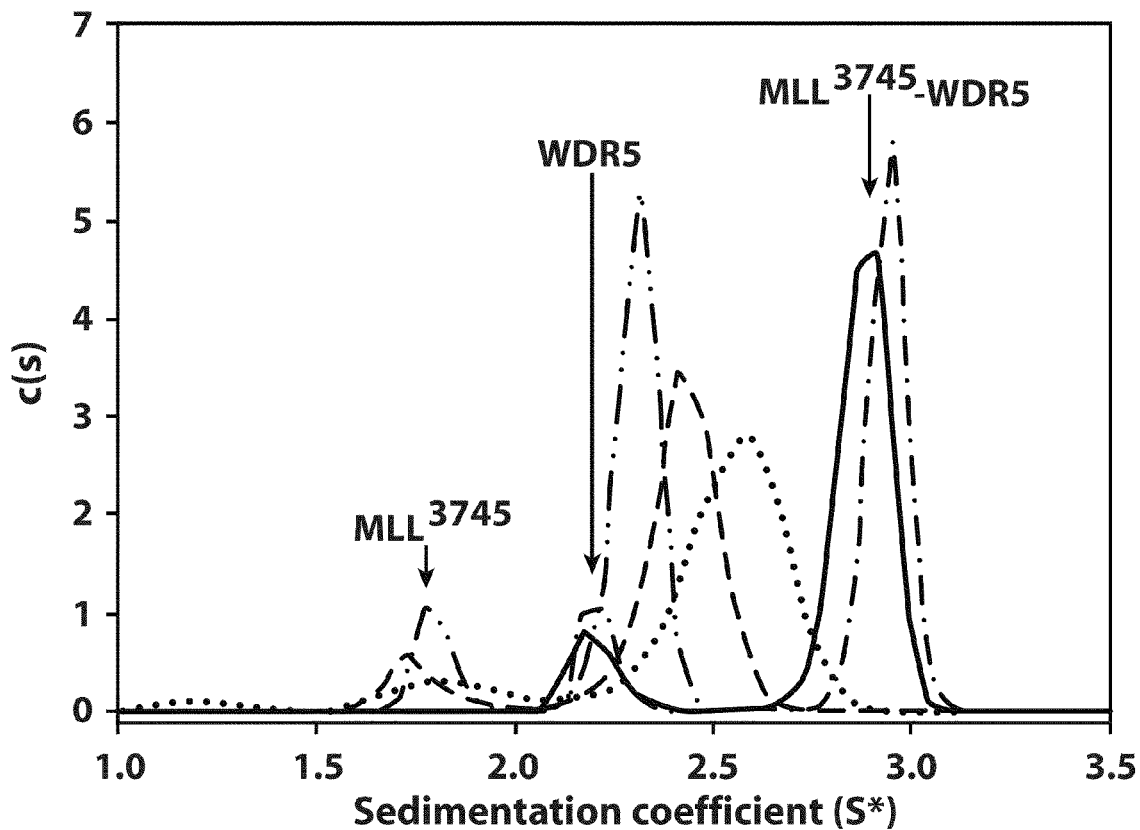
FIG. 8 shows the effect of a MLL1 Win peptide on the interaction between $MLL^{3745}$ and WDR5.

To determine whether the peptide disclosed herein can inhibit the assembly and activity of the MLL1 core complex in vitro, we compared sedimentation velocity profiles and enzymatic activity of the MLL1 core complex in the presence and absence of increasing amounts of the MLL1 Win peptide. See FIG. 8. We used the arginine-containing tumor suppressor p53 ($^{365}$HSSHLKSKKGQSTSRHKK$^{382}$, SEQ ID NO. 27) as a control. The addition of a 20-, 30-, and 60-fold stoichiometric excess of the MLL1 Win peptide (SEQ ID NO. 24) caused the 5 s* sedimentation peak of the MLL1 core complex to increasingly broaden and shift to lower sedimentation values. For example, at a 60-fold excess of the MLL1 Win peptide, the sedimentation profile of the complex was significantly broadened with a peak at 4.6 s*, similar to that observed with complexes assembled with the F133A WDR5 protein. This is consistent with a model in which the MLL1 Win peptide competes with MLL1 for binding to the WDR5 component of the WDR5-RbBP5-Ash2L subcomplex, producing a broad c(s) peak intermediate between the 4 s* subcomplex and the 5 s* holocomplex that is not resolvable within the signal-to-noise ratio of the data.

Figure 7A:
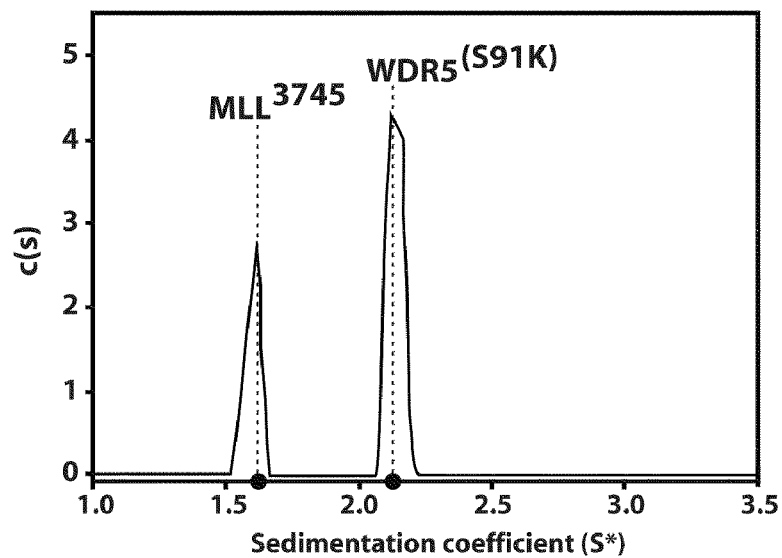
FIG. 7A and FIG. 7B show the sedimentation velocity data for the interaction of point-mutated WDR5 polypeptides with $MLL^{3745}$ protein.
Figure 7B:
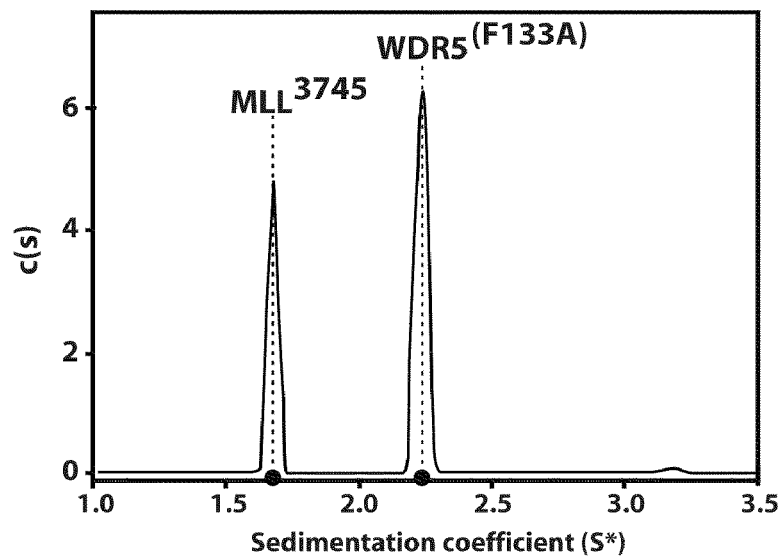

X-ray structural studies of WDR5 bound to histone H3 peptides revealed that arginine-2 of histone H3 is critical for the interaction with WDR5. The side chain of H3R2 inserts into a central cavity of WDR5 and is stabilized by hydrogen bond, hydrophobic, and cation-π interactions. Since the sequence surrounding Arg-3765 of MLL1 is similar to that surrounding Arg-2 of H3, we hypothesized that WDR5 interacts with MLL1 by a similar mechanism. To test this hypothesis, we constructed point mutations in WDR5 and analyzed the mutant proteins for their ability to interact with wild-type MLL$^{3745}$ in sedimentation velocity experiments. It was previously reported that the S91K and F133A WDR5 mutations prevent histone H3 binding to free WDR5. Both Ser-91 and Phe-133 line the surface of the central arginine binding cavity, and the replacement of Ser-91 with lysine is expected to sterically interfere with the insertion of the arginine side chain into the cavity. Phe-133 makes extensive hydrophobic and cation-π interactions with the guanidinium of arginine and was previously shown to be critical for the interaction of histone H3 with WDR5. We observed that both the S91K and the F133A WDR5 proteins are incapable of interacting with MLL3745 in sedimentation velocity experiments (FIGS. 7A and 7B). This occurs without significant changes in the frictional coefficient or CD spectra of either mutant protein, suggesting that the overall conformation of the S91K and F133A mutant proteins is similar to that of wild-type WDR5. These results suggest that the central arginine binding cavity of WDR5 is important for the interaction with SET1 proteins.

Figure 9A:
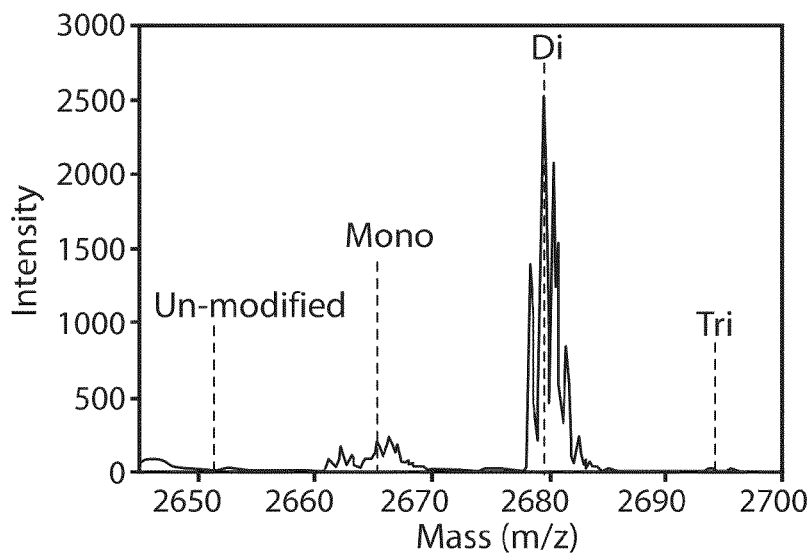
FIGS. 9A to 9F shows the effect of a Win peptide on the dimethylation activity of the MLL1 core complex.
Figure 9B:
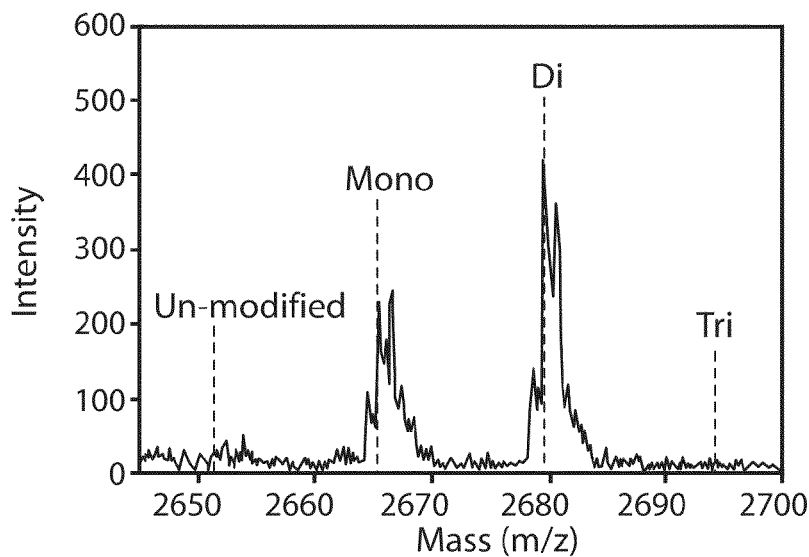
Figure 9C:
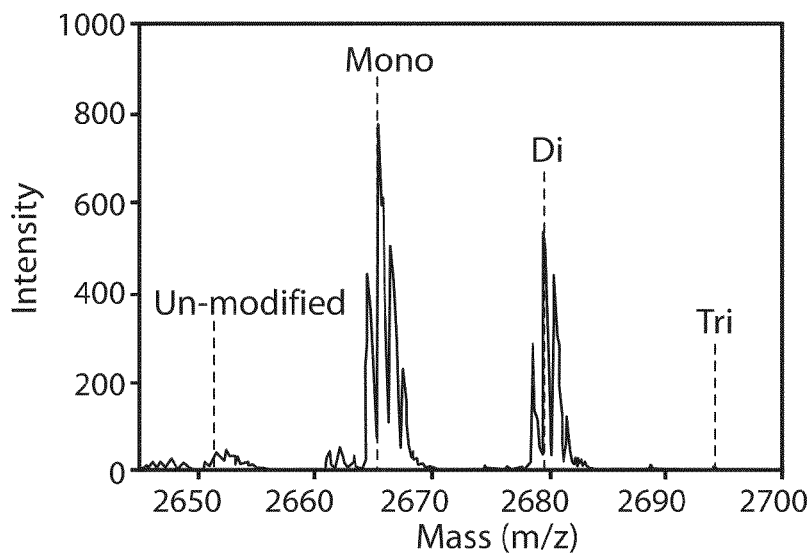
Figure 9D:
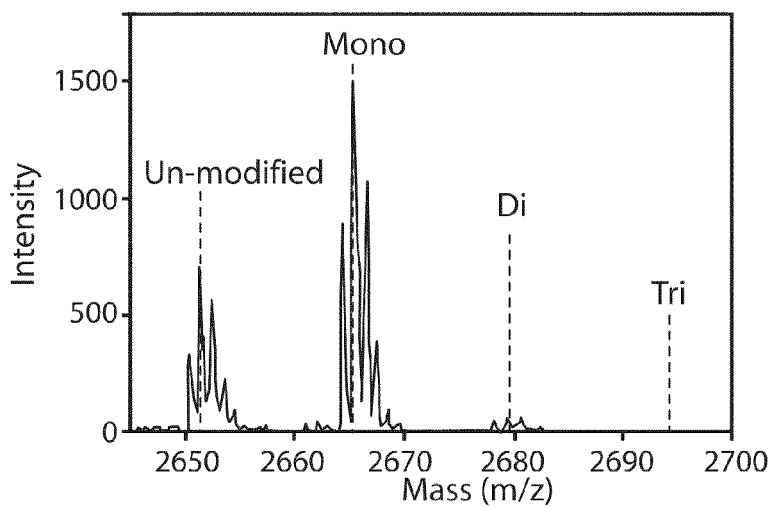
Figure 9E:
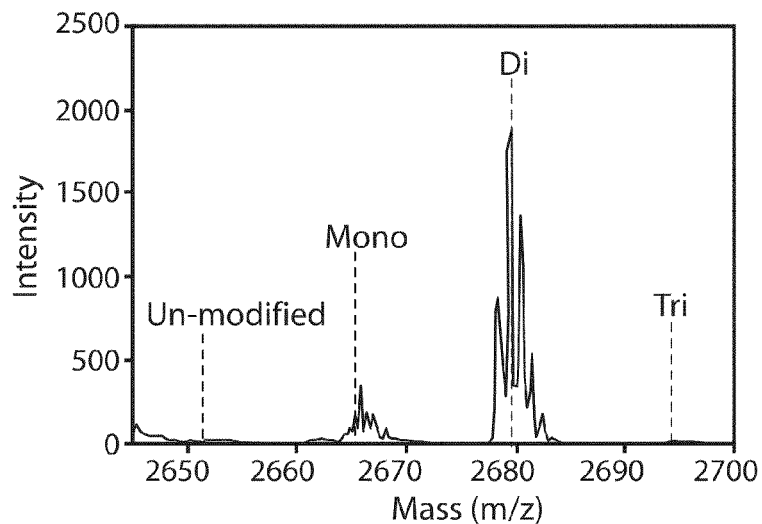
Figure 9F:
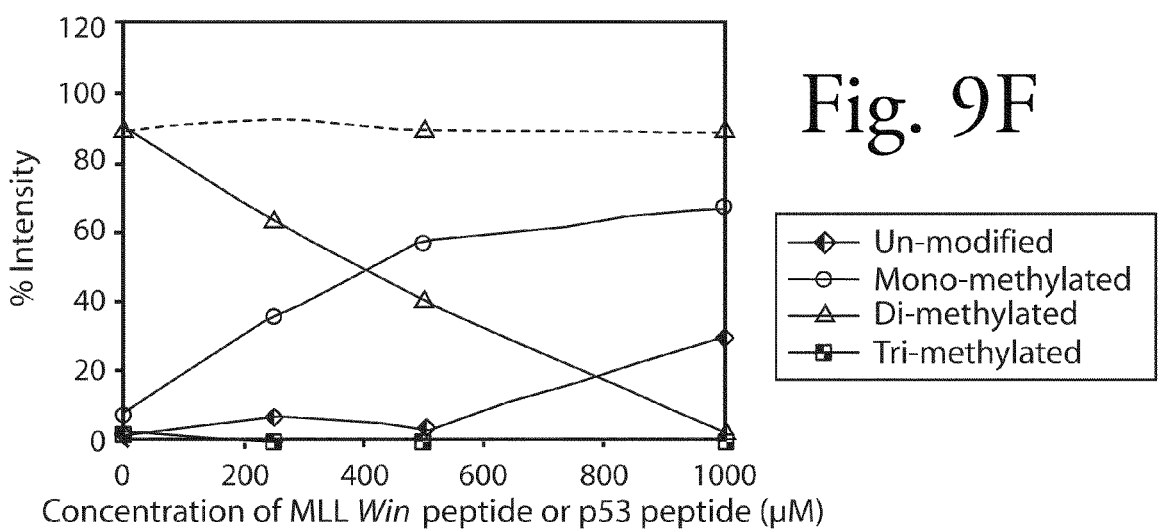

Consistent with these observations, we have seen a loss of H3K4 dimethylation activity of the MLL1 core complex when Arg-3765 of the MLL1 component is replaced by an alanine. See FIG. 9. Instead of dimethylation activity, only monomethylation activity is seen, which is the normal activity of MLL1 when it is not part of a core complex. Sedimentation analysis of the MLL1 (R3765A) variant, when combined with WDR5, RbBP5 and Ash2L, showed the complex was not formed. The MLL1 Win motif peptide inhibits the H3K4 dimethylation activity of the MLL1 core complex. FIGS. 9a-e, show data for the MALDI-TOF mass spectrometry of enzymatic activity catalyzed by the wild-type MLL1 core complex in the absence (9a) or presence (9b-d) of an excess of the peptide. FIG. 9B shows a 20-fold excess. FIG. 9C shows a 30-fold excess. FIG. 9D shows a 60-fold stoichiometric excess of MLL1 Win peptide. Mono, monomethylation; Di, dimethylation; Tri, trimethylation is illustrated in FIG. 9E. MALDI-TOF mass spectrometry of enzymatic assay catalyzed by wild-type MLL1 core complex in the presence of a 60-fold molar excess of the p53 peptide is shown in FIG. 9F.

Methods

Protein Expression and Purification—A human spleen c-DNA library was used to amplify an MLL1 C-terminal fragment encoding residues 3592-3969. PCR subcloning was used to amplify MLL1 SET domain constructs consisting of residues 3745-3969 (MLL$^{3745}$) and residues 3811-3969 (MLL$^{3811}$). MLL$^{3745}$ and MLL$^{3811}$ were ligated into the pGST and pMBP parallel vectors, respectively. pMCGS7 plasmids encoding full-length WDR5 as N-terminal His6 fusions were obtained as generous gifts from Alexander Ruthenburg and David Allis. A plasmid containing the RbBP5 clone was obtained as a generous gift from Yali Dou and was subcloned into the pET3a vector without affinity tags. The ash2L gene (Clone ID 3921999) was purchased from Open Biosystems and subcloned into the pHis Parallel vector, which encodes tobacco etch virus (TEV) 3 cleavable N-terminal His6 fusion.

All recombinant proteins were overexpressed in *Escherichia coli* (Rosetta II, Novagen) by growing cells containing the plasmids at 37° C. in Terrific Broth medium containing 50 μg/ml carbenicillin to an $A_{600}$ of 1.0. The temperature was then lowered to 16° C., and cells were induced with isopropyl-1-thio-β-D-galactopyranoside (0.1-1 mM) for 16-18 h. RbBP5 and Ash2L were induced with 0.1 mM and 0.25 mM isopropyl-1-thio-β-D-galactopyranoside, respectively. Cells were harvested, re-suspended in lysis buffer (50 mM Tris, pH 7.3, 300 mM NaCl, 10% glycerol, 3 mM dithiothreitol, 0.1 mM phenylmethylsulfonyl fluoride, and EDTA-free protease inhibitor mixture (Roche Applied Science), lysed with a microfluidizer cell disrupter, and clarified by centrifugation. Cells containing the RbBP5 plasmid were lysed instead using the same lysis buffer containing 1× BugBuster® (Novagen), which minimized RbBP5 degradation upon cell lysis. Clarified supernatants containing the GST-MLL$^{3745}$ protein were passed over a glutathione-Sepharose column (GSTrap™ FF column, GE-Healthcare), and GST-MLL$^{3745}$ was eluted with a gradient of reduced glutathione. Fractions containing GST-MLL$^{3745}$ were combined, treated with TEV protease, and dialyzed with three changes against lysis buffer (without protease inhibitors). MLL$^{3745}$ was further purified over a glutathione-Sepharose column followed by gel filtration chromatography. MBP-MLL$^{3811}$ fusion protein was purified by amylose affinity chromatography followed by TEV protease treatment and two rounds of gel filtration chromatography. Full-length WDR5 protein was expressed and purified as described previously. RbBP5 protein was purified by ion exchange and gel filtration chromatography. Ash2L was purified by nickel affinity chromatography (HisTrap column, GE Healthcare), dialysis and TEV cleavage to remove imidazole and the His6 tag, and repurification over a His-trap column. As a final step of purification and for buffer exchange, all proteins were passed through a gel filtration column (Superdex 200, GE Healthcare) pre-equilibrated with 20 mM Tris (pH 7.5), 300 mM NaCl, 1 mM TCEP, and 1 µM ZnCl$_2$.

Mutagenesis and Peptides—Point mutations were introduced into MLL1 and WDR5 constructs using the QuikChange site-directed mutagenesis kit (Stratagene). Plasmids were sequenced to verify the presence of the intended mutations and the absence of additional mutations. Peptides were synthesized by Global Peptide and Genscript.

Analytical Ultracentrifugation—Analytical ultracentrifugation experiments were carried out using a Beckman Coulter ProteomeLab™ XL-A analytical ultracentrifuge equipped with absorbance optics and an eight-hole An-50 Ti analytical rotor. Sedimentation velocity experiments were carried out at 10° C. and 50,000 rpm (200,000×g) using 3-mm two-sector charcoal filled Epon centerpieces with quartz windows. Each sample was scanned at 0-min time intervals for 300 scans. Protein samples in 20 mM Tris-Cl, pH 7.5, 300 mM NaCl, 1 mM TCEP, and 1 µM ZnCl$_2$ were run at various concentrations, and molar ratios were as described under "Results." Sedimentation boundaries were analyzed by the continuous distribution (c(s)) method using the program SEDFIT. Equilibrium dissociation constants for WDR5-MLL1 complexes were obtained by global fitting sedimentation velocity data acquired at several different protein concentrations using the single-site hetero-association model (A+B↔_9 AB) of SEDPHAT. The program SEDNTERP, version 1.09, was used to correct the experimental s value (s*) to standard conditions at 20° C. in water ($s_{20}$,w) and to calculate the partial specific volume of each protein.

Methyltransferase Assays—Radiolabeling assays were conducted by combining 7 µg of MLL$^{3745}$ or MLL$^{3811}$ with 500 µM histone H3 peptide containing residues 1-20 (with GGK-biotin on the C terminus) and 1 µCi of [3H]methyl-S-adenosyl-methionine (GE Healthcare) in 50 mM Tris, pH 8.5, 200 mM NaCl, 3 mM dithiothreitol, 5 mM MgCl$_2$, and 5% glycerol. The reactions were incubated at 15° C. for 2 h, stopped by the addition of SDS-loading buffer to 1×, and separated by SDS-PAGE on a 4-12% gradient gel (Invitrogen). The gel then was soaked in an autoradiography enhancer solution (Enlightning, PerkinElmer Life Sciences), dried, and exposed to film at −80° C. for 24 h.

Mass spectrometry assays were conducted by adapting that previously reported for Dim5 and SET7/9 histone methyltransferases. Six micrograms of MLL$^{3745}$ or MLL1 core complex was incubated with 250 µM s-adenosyl-methionine and 10 µM histone H3 peptide (amino acid residues 1-20) at 15° C. in 50 mM Tris-Cl, pH 9.0, 200 mM NaCl, 3 mM dithiothreitol, and 5% glycerol. The reactions were quenched at various time points by the addition of trifluoroacetic acid to 0.5%. The quenched samples were diluted 1:4 with α-cyano-4-hydroxycinnamic acid. MALDI-TOF mass spectrometry was performed on a Bruker AutoFlex mass spectrometer (State University of New York (SUNY), Oswego, N.Y.) operated in reflectron mode. Final spectra were averaged from 100 shots/position at 10 different positions.

Circular Dichroism Spectroscopy—CD spectra were collected on an AVIV 62A DS spectropolarimeter equipped with a Neslab CFT-33 refrigerated circulator at 10° C. using a 0.1-mm path length cell. Spectra for each protein at a concentration of 0.2 mg/ml were collected in a buffer containing 10 mM Tris (pH 7.5), 200 mM NaCl, 1 mM TCEP, and 1 µM ZnCl$_2$. The background contribution of the buffer alone was subtracted from each protein spectrum.

Crystallization and Structure Determination—An N-terminally truncated form of WDR5 (residues 23-335, ΔN-WDR5) was expressed and purified as described previously. As a final step of purification and for buffer exchange, all proteins were passed through a gel filtration column pre-equilibrated with 20 mM Tris (7.5), 300 mM NaCl, 1 mM (tris(2-carboxyethyl)phosphine, and 1 µM ZnCl$_2$. The protein was concentrated to 9 mg/ml and mixed with a stock solution of the MLL1 Win peptide SEQ ID NO. 24 ($_{acetyl}$GSARAE-VHLRKS$_{NH2}$) dissolved in the same buffer. The final concentration of ΔN-WDR5 and peptide was 8.2 mg/ml and 0.9 mM, respectively. The hanging drop vapor diffusion method was used for crystallization, using as mother liquor 30 mM ammonium sulfate, 30% (w/v) polyethylene glycol-3350, and 100 mM HEPES (pH 7.5). Crystals were flashfrozen in mother liquor containing 40% polyethylene glycol-3350. Diffraction data were collected at the National Synchrotron Light Source (NSLS) on beamline X6A. Data were collected with a Quantum 210 CCD detector and reduced with HKL-2000 and CCP4. The MLL1 Win peptide-WDR5 complex structure was determined by molecular replacement with MOLREP using the coordinates of the previously determined structure of WDR5 (PDB code: 2H68) as a search model. After an initial rigid body refinement, the structure was further refined with rounds of simulated annealing, energy minimization, and individual B-factor refinement with a maximum likelihood target using CNS. Difference Fourier maps were calculated with CNS and used to locate electron density corresponding to bound peptide, and the structure was built using O. The peptide position was verified with simulated annealing omit maps. All structural figures were generated with PyMOL.

Isothermal Titration Calorimetry—Isothermal titration calorimetry (ITC) experiments were performed using VP-ITC calorimeter (MicroCal). All experiments were performed at 20° C. in a sample buffer containing 20 mM Tris (pH 7.5), 150 mM sodium chloride, and 1 mM (tris(2-carboxyethyl)phosphine. A 0.05 mM solution of full-length WDR5 diluted in sample buffer was placed in the sample cell, and a 0.45 mM solution of peptide made up in sample buffer was loaded into the injection syringe. For each experiment, a 180-s delay at the start of the experiment was followed by 30 injections of 10 µl of the titrant solution, spaced 300 s apart. The sample was stirred at 300 rpm throughout. Blank injections of the peptide into buffer were subtracted from the experimental titrations, and binding isotherms were fit to a theoretical titration curve describing one binding site per titrant. A nonlinear best-fit binding isotherm for the data was used to calculate the protein-titrant stoichiometry, dissociation constant, and standard change in enthalpy using the supplied manufacturer's software Origin 7.0 (Origin-Lab Corp.).

While the subject matter has been described with reference to certain embodiments, it will be understood by those skilled in the art that various changes may be made and equivalents may be substituted for elements thereof to adapt to particular situations without departing from the scope of the claims. Therefore, it is intended that the claims not be limited to the particular embodiments disclosed as the best mode contemplated, but will include all embodiments falling within the scope and spirit of the appended claims.

What is claimed is:

1. A method for inhibiting the histone 3 lysine 4 of (H3K4) dimethylation activity of a Suppressor of variegation Enhancer of Zeste, Trithorax (SET1) protein core complex comprising the steps of exposing a peptide to a cell comprising both a tryptophan-aspartic acid repeat 5 (WDR5) and a SET1 family protein, wherein the WDR5 and SET1 family protein are components of a SET1 family core complex that has histone 3 lysine 4 dimethylation (H3K4) activity when exposed to histone protein H3, the WDR5 having a SET receptor site (N-SET) that is N-terminal to a SET domain; wherein the peptide has fewer than twenty residues that includes SEQ ID NO. 7 where $X_1$ is one of S, C and A, $X_2$ is one of A and S and $X_3$ is one of A and E; and inhibiting the H3K4 dimethylation activity of the SET1 family core complex by allowing the peptide and the WDR5 to bind such that the peptide blocks the N-SET receptor site of WDR5, thus inhibiting the formation of the SET1 family core complex, the inhibition being relative to an identical sample that lacks the peptide.

2. The method as recited in claim 1, wherein the peptide has fewer than fifteen residues.

3. The method as recited in claim 1, wherein the peptide includes the structure recited in SEQ ID NO. 13.

4. The method as recited in claim 1, wherein the step of inhibiting the H3k4 dimethylation activity inhibits the activity to a degree that is dependent on the dose of the peptide.

5. The method as recited in claim 1, wherein the step of inhibiting the H3K4 dimethylation activity inhibits the activity to a degree that reduces the dimethylation activity by at least 10% after 24 hours according to a methyltransferase assay performed at 15° C. for 2 h.

6. The method as recited in claim 1, wherein $X_1$ is C, $X_2$ is S and $X_3$ is E.

7. The method as recited in claim 1, wherein the peptide consists of a structure selected from the group consisting of SEQ ID NO. 9, SEQ ID NO. 10, SEQ ID NO.11, SEQ ID NO. 12, SEQ ID NO.13 and SEQ ID NO 14.

8. The method as recited in claim 1, wherein the peptide includes the structure recited in SEQ ID NO. 15 where $X_1$ is one of S, C and A, $X_2$ one of A and S, $X_3$ is one of A and E, $X_4$ is one of V, P and G and $X_5$ is one of H, Y, F and K.

9. The method as recited in claim 8, wherein the peptide includes the structure recited in SEQ ID NO. 21.

10. The method as recited in claim 8, wherein the peptide consists of the structure recited in SEQ ID NO. 19.

\* \* \* \* \*

SEQUENCE LISTING

<160> NUMBER OF SEQ ID NOS: 27

<210> SEQ ID NO 1
<211> LENGTH: 22
<212> TYPE: PRT
<213> ORGANISM: Artificial Sequence
<220> FEATURE:
<223> OTHER INFORMATION: Completely synthetic protein fragment of
      MLL1 from homo sapien

<400> SEQUENCE: 1

Asn Glu Pro Pro Leu Asn Pro His Gly Ser Ala Arg Ala Glu Val His
1               5                   10                  15

Leu Arg Lys Ser Ala Phe
            20

<210> SEQ ID NO 2
<211> LENGTH: 22
<212> TYPE: PRT
<213> ORGANISM: Artificial Sequence
<220> FEATURE:
<223> OTHER INFORMATION: Completely synthetic protein fragment of MLL2
      from homo sapien

<400> SEQUENCE: 2

Leu Pro Leu Met Ile Asn Pro Thr Gly Cys Ala Arg Ser Glu Pro Lys
1               5                   10                  15

Ile Leu Thr His Tyr Lys
            20

<210> SEQ ID NO 3
<211> LENGTH: 22
<212> TYPE: PRT
<213> ORGANISM: Artificial Sequence
<220> FEATURE:
<223> OTHER INFORMATION: Completely synthetic protein fragment of MLL3
      from homo sapien

<400> SEQUENCE: 3

Leu Pro Leu Ala Val Asn Pro Thr Gly Cys Ala Arg Ser Glu Pro Lys
1               5                   10                  15

Met Ser Ala His Val Lys
            20

<210> SEQ ID NO 4
<211> LENGTH: 22
<212> TYPE: PRT
<213> ORGANISM: Artificial Sequence
<220> FEATURE:
<223> OTHER INFORMATION: Completely synthetic protein fragment of
      MLL4 from homo sapien

<400> SEQUENCE: 4

Glu Glu Pro Pro Leu Asn Pro His Gly Ala Ala Arg Ala Glu Val Tyr
1               5                   10                  15

Leu Arg Lys Cys Thr Phe
            20

<210> SEQ ID NO 5
<211> LENGTH: 22
<212> TYPE: PRT
<213> ORGANISM: Artificial Sequence
<220> FEATURE:
<223> OTHER INFORMATION: Completely synthetic protein fragment of
      SET1a from homo sapien

```
<400> SEQUENCE: 5

Asp Gly Pro Arg Glu His Gln Thr Gly Ser Ala Arg Ser Glu Gly Tyr
1               5                   10                  15

Tyr Pro Ile Ser Lys Lys
            20

<210> SEQ ID NO 6
<211> LENGTH: 22
<212> TYPE: PRT
<213> ORGANISM: Artificial Sequence
<220> FEATURE:
<223> OTHER INFORMATION: Completely synthetic protein fragment of
      SET1b from homo sapien

<400> SEQUENCE: 6

Asp Gly Ile Arg Glu His Val Thr Gly Cys Ala Arg Ser Glu Gly Phe
1               5                   10                  15

Tyr Thr Ile Asp Lys Lys
            20

<210> SEQ ID NO 7
<211> LENGTH: 6
<212> TYPE: PRT
<213> ORGANISM: Artificial Sequence
<220> FEATURE:
<223> OTHER INFORMATION: Completely synthetic protein fragment based
      on SET1 family core complex from homo sapien
<220> FEATURE:
<221> NAME/KEY: VARIANT
<222> LOCATION: (2)..(2)
<223> OTHER INFORMATION: S, C or A
<220> FEATURE:
<221> NAME/KEY: VARIANT
<222> LOCATION: (5)..(5)
<223> OTHER INFORMATION: A or S
<220> FEATURE:
<221> NAME/KEY: VARIANT
<222> LOCATION: (6)..(6)
<223> OTHER INFORMATION: A or E

<400> SEQUENCE: 7

Gly Xaa Ala Arg Xaa Xaa
1               5

<210> SEQ ID NO 8
<211> LENGTH: 7
<212> TYPE: PRT
<213> ORGANISM: Artificial Sequence
<220> FEATURE:
<223> OTHER INFORMATION: Completely synthetic protein fragment based
      on SET1 family core complex from homo sapien
<220> FEATURE:
<221> NAME/KEY: VARIANT
<222> LOCATION: (1)..(1)
<223> OTHER INFORMATION: H or T
<220> FEATURE:
<221> NAME/KEY: VARIANT
<222> LOCATION: (3)..(3)
<223> OTHER INFORMATION: S, C or A
<220> FEATURE:
<221> NAME/KEY: VARIANT
<222> LOCATION: (6)..(6)
<223> OTHER INFORMATION: A or S
<220> FEATURE:
<221> NAME/KEY: VARIANT
<222> LOCATION: (7)..(7)
<223> OTHER INFORMATION: A or E

<400> SEQUENCE: 8

Xaa Gly Xaa Ala Arg Xaa Xaa
```

-continued

```
<210> SEQ ID NO 9
<211> LENGTH: 6
<212> TYPE: PRT
<213> ORGANISM: Artificial Sequence
<220> FEATURE:
<223> OTHER INFORMATION: Completely synthetic protein fragment based
      on SET1 family core complex from homo sapien

<400> SEQUENCE: 9

Gly Ser Ala Arg Ala Glu
1               5

<210> SEQ ID NO 10
<211> LENGTH: 6
<212> TYPE: PRT
<213> ORGANISM: Artificial Sequence
<220> FEATURE:
<223> OTHER INFORMATION: Completely synthetic protein fragment based
      on SET1 family core complex from homo sapien

<400> SEQUENCE: 10

Gly Ser Ala Arg Ala Ala
1               5

<210> SEQ ID NO 11
<211> LENGTH: 6
<212> TYPE: PRT
<213> ORGANISM: Artificial Sequence
<220> FEATURE:
<223> OTHER INFORMATION: Completely synthetic protein fragment based
      on SET1 family core complex from homo sapien

<400> SEQUENCE: 11

Gly Cys Ala Arg Ser Glu
1               5

<210> SEQ ID NO 12
<211> LENGTH: 6
<212> TYPE: PRT
<213> ORGANISM: Artificial Sequence
<220> FEATURE:
<223> OTHER INFORMATION: Completely synthetic protein fragment based
      on SET1 family core complex from homo sapien

<400> SEQUENCE: 12

Gly Ala Ala Arg Ala Glu
1               5

<210> SEQ ID NO 13
<211> LENGTH: 6
<212> TYPE: PRT
<213> ORGANISM: Artificial Sequence
<220> FEATURE:
<223> OTHER INFORMATION: Completely synthetic protein fragment based
      on SET1 family core complex from homo sapien

<400> SEQUENCE: 13

Gly Ser Ala Arg Ser Glu
1               5

<210> SEQ ID NO 14
<211> LENGTH: 6
<212> TYPE: PRT
<213> ORGANISM: Artificial Sequence
<220> FEATURE:
<223> OTHER INFORMATION: Completely synthetic protein fragment based
      on SET1 family core complex from homo sapien
```

```
<400> SEQUENCE: 14

Gly Cys Ala Arg Ser Glu
1               5

<210> SEQ ID NO 15
<211> LENGTH: 8
<212> TYPE: PRT
<213> ORGANISM: Artificial Sequence
<220> FEATURE:
<223> OTHER INFORMATION: Completely synthetic protein fragment based
      on SET1 family core complex from homo sapien
<220> FEATURE:
<221> NAME/KEY: VARIANT
<222> LOCATION: (2)..(2)
<223> OTHER INFORMATION: S, C or A
<220> FEATURE:
<221> NAME/KEY: VARIANT
<222> LOCATION: (5)..(5)
<223> OTHER INFORMATION: A or S
<220> FEATURE:
<221> NAME/KEY: VARIANT
<222> LOCATION: (6)..(6)
<223> OTHER INFORMATION: A or E
<220> FEATURE:
<221> NAME/KEY: VARIANT
<222> LOCATION: (7)..(7)
<223> OTHER INFORMATION: V, P or G
<220> FEATURE:
<221> NAME/KEY: VARIANT
<222> LOCATION: (8)..(8)
<223> OTHER INFORMATION: H, Y, F or K

<400> SEQUENCE: 15

Gly Xaa Ala Arg Xaa Xaa Xaa Xaa
1               5

<210> SEQ ID NO 16
<211> LENGTH: 8
<212> TYPE: PRT
<213> ORGANISM: Artificial Sequence
<220> FEATURE:
<223> OTHER INFORMATION: Completely synthetic protein fragment based
      on SET1 family core complex from homo sapien
<220> FEATURE:
<221> NAME/KEY: VARIANT
<222> LOCATION: (2)..(2)
<223> OTHER INFORMATION: S, C or A
<220> FEATURE:
<221> NAME/KEY: VARIANT
<222> LOCATION: (5)..(5)
<223> OTHER INFORMATION: A or S
<220> FEATURE:
<221> NAME/KEY: VARIANT
<222> LOCATION: (6)..(6)
<223> OTHER INFORMATION: A or E
<220> FEATURE:
<221> NAME/KEY: VARIANT
<222> LOCATION: (7)..(7)
<223> OTHER INFORMATION: V, P or G
<220> FEATURE:
<221> NAME/KEY: VARIANT
<222> LOCATION: (8)..(8)
<223> OTHER INFORMATION: H, Y or F

<400> SEQUENCE: 16

Gly Xaa Ala Arg Xaa Xaa Xaa Xaa
1               5

<210> SEQ ID NO 17
<211> LENGTH: 8
<212> TYPE: PRT
<213> ORGANISM: Artificial Sequence
<220> FEATURE:
```

```
<223> OTHER INFORMATION: Completely synthetic protein fragment based
      on SET1 family core complex from homo sapien
<220> FEATURE:
<221> NAME/KEY: VARIANT
<222> LOCATION: (2)..(2)
<223> OTHER INFORMATION: S, C or A
<220> FEATURE:
<221> NAME/KEY: VARIANT
<222> LOCATION: (5)..(5)
<223> OTHER INFORMATION: A or S
<220> FEATURE:
<221> NAME/KEY: VARIANT
<222> LOCATION: (6)..(6)
<223> OTHER INFORMATION: A or E
<220> FEATURE:
<221> NAME/KEY: VARIANT
<222> LOCATION: (7)..(7)
<223> OTHER INFORMATION: V, P or G

<400> SEQUENCE: 17

Gly Xaa Ala Arg Xaa Xaa Xaa Lys
1               5

<210> SEQ ID NO 18
<211> LENGTH: 9
<212> TYPE: PRT
<213> ORGANISM: Artificial Sequence
<220> FEATURE:
<223> OTHER INFORMATION: Completely synthetic protein fragment based
      on SET1 family core complex from homo sapien

<400> SEQUENCE: 18

Gly Ser Ala Arg Ala Glu Val His Leu
1               5

<210> SEQ ID NO 19
<211> LENGTH: 8
<212> TYPE: PRT
<213> ORGANISM: Artificial Sequence
<220> FEATURE:
<223> OTHER INFORMATION: Completely synthetic protein fragment based
      on SET1 family core complex from homo sapien

<400> SEQUENCE: 19

Gly Cys Ala Arg Ser Glu Pro Lys
1               5

<210> SEQ ID NO 20
<211> LENGTH: 8
<212> TYPE: PRT
<213> ORGANISM: Artificial Sequence
<220> FEATURE:
<223> OTHER INFORMATION: Completely synthetic protein fragment based
      on SET1 family core complex from homo sapien

<400> SEQUENCE: 20

Gly Ala Ala Arg Ala Glu Val Tyr
1               5

<210> SEQ ID NO 21
<211> LENGTH: 8
<212> TYPE: PRT
<213> ORGANISM: Artificial Sequence
<220> FEATURE:
<223> OTHER INFORMATION: Completely synthetic protein fragment based
      on SET1 family core complex from homo sapien

<400> SEQUENCE: 21

Gly Ser Ala Arg Ser Glu Gly Tyr
1               5
```

```
<210> SEQ ID NO 22
<211> LENGTH: 8
<212> TYPE: PRT
<213> ORGANISM: Artificial Sequence
<220> FEATURE:
<223> OTHER INFORMATION: Completely synthetic protein fragment based
      on SET1 family core complex from homo sapien

<400> SEQUENCE: 22

Gly Cys Ala Arg Ser Glu Gly Phe
1               5

<210> SEQ ID NO 23
<211> LENGTH: 8
<212> TYPE: PRT
<213> ORGANISM: Artificial Sequence
<220> FEATURE:
<223> OTHER INFORMATION: Completely synthetic protein fragment based
      on SET1 family core complex from homo sapien
<220> FEATURE:
<221> NAME/KEY: VARIANT
<222> LOCATION: (2)..(2)
<223> OTHER INFORMATION: S, C or A
<220> FEATURE:
<221> NAME/KEY: VARIANT
<222> LOCATION: (5)..(5)
<223> OTHER INFORMATION: A or S
<220> FEATURE:
<221> NAME/KEY: VARIANT
<222> LOCATION: (7)..(7)
<223> OTHER INFORMATION: V, P or G
<220> FEATURE:
<221> NAME/KEY: VARIANT
<222> LOCATION: (8)..(8)
<223> OTHER INFORMATION: H, Y, F or K

<400> SEQUENCE: 23

Gly Xaa Ala Arg Xaa Glu Xaa Xaa
1               5

<210> SEQ ID NO 24
<211> LENGTH: 12
<212> TYPE: PRT
<213> ORGANISM: Artificial Sequence
<220> FEATURE:
<223> OTHER INFORMATION: Completely synthetic protein fragment based
      on SET1 family core complex from homo sapien

<400> SEQUENCE: 24

Gly Ser Ala Arg Ala Glu Val His Leu Arg Lys Ser
1               5                   10

<210> SEQ ID NO 25
<211> LENGTH: 6
<212> TYPE: PRT
<213> ORGANISM: Artificial Sequence
<220> FEATURE:
<223> OTHER INFORMATION: Completely synthetic protein fragment based
      on SET1 family core complex from homo sapien

<400> SEQUENCE: 25

Gly Ser Ala Arg Ala Glu
1               5

<210> SEQ ID NO 26
<211> LENGTH: 225
<212> TYPE: PRT
<213> ORGANISM: Artificial Sequence
<220> FEATURE:
<223> OTHER INFORMATION: Residues 3745-3969 of MLL1 from homo sapien
```

```
<400> SEQUENCE: 26

Phe Arg Phe His Lys Pro Glu Glu Ala Asn Glu Pro Pro Leu Asn Pro
1               5                   10                  15

His Gly Ser Ala Arg Ala Glu Val His Leu Arg Lys Ser Ala Phe Asp
            20                  25                  30

Met Phe Asn Phe Leu Ala Ser Lys His Arg Gln Pro Pro Glu Tyr Asn
        35                  40                  45

Pro Asn Asp Glu Glu Glu Glu Val Gln Leu Lys Ser Ala Arg Arg
    50                  55                  60

Ala Thr Ser Met Asp Leu Pro Met Pro Met Arg Phe Arg His Leu Lys
65              70                  75                  80

Lys Thr Ser Lys Glu Ala Val Gly Val Tyr Arg Ser Pro Ile His Gly
                85                  90                  95

Arg Gly Leu Phe Cys Lys Arg Asn Ile Asp Ala Gly Glu Met Val Ile
            100                 105                 110

Glu Tyr Ala Gly Asn Val Ile Arg Ser Ile Gln Thr Asp Lys Arg Glu
            115                 120                 125

Lys Tyr Tyr Asp Ser Lys Gly Ile Gly Cys Tyr Met Phe Arg Ile Asp
    130                 135                 140

Asp Ser Glu Val Val Asp Ala Thr Met His Gly Asn Ala Ala Arg Phe
145                 150                 155                 160

Ile Asn His Ser Cys Glu Pro Asn Cys Tyr Ser Arg Val Ile Asn Ile
            165                 170                 175

Asp Gly Gln Lys His Ile Val Ile Phe Ala Met Arg Lys Ile Tyr Arg
            180                 185                 190

Gly Glu Glu Leu Thr Tyr Asp Tyr Lys Phe Pro Ile Glu Asp Ala Ser
        195                 200                 205

Asn Lys Leu Pro Cys Asn Cys Gly Ala Lys Lys Cys Arg Lys Phe Leu
    210                 215                 220

Asn
225

<210> SEQ ID NO 27
<211> LENGTH: 18
<212> TYPE: PRT
<213> ORGANISM: Artificial Sequence
<220> FEATURE:
<223> OTHER INFORMATION: Completely synthetic fragment of the p53
      tumor suppressor protein from homo sapiens

<400> SEQUENCE: 27

His Ser Ser His Leu Lys Ser Lys Lys Gly Gln Ser Thr Ser Arg His
1               5                   10                  15

Lys Lys
```